United States Patent [19]
Simpson et al.

[11] Patent Number: 6,117,147
[45] Date of Patent: Sep. 12, 2000

[54] DEVICE AND METHOD FOR REINFORCING AN ANASTOMOTIC SITE

[75] Inventors: Charles Lee Simpson; Brian K. McIlroy, both of Austin, Tex.

[73] Assignee: Sulzer Carbomedics Inc., Austin, Tex.

[21] Appl. No.: 09/164,145

[22] Filed: Sep. 30, 1998

[51] Int. Cl.[7] .................................................. A61B 17/08
[52] U.S. Cl. ............................................................ 606/153
[58] Field of Search ..................................... 606/151, 153

[56] References Cited

U.S. PATENT DOCUMENTS

| | | | |
|---|---|---|---|
| 3,774,615 | 11/1973 | Lim et al. | 128/344 C |
| 3,818,515 | 6/1974 | Neville | 3/1 |
| 4,368,736 | 1/1983 | Kaster | 128/334 C |
| 4,523,592 | 6/1985 | Daniel | 128/334 C |
| 4,607,637 | 8/1986 | Berggren et al. | 128/334 C |
| 4,907,591 | 3/1990 | Vasconcellos et al. | 606/154 |
| 5,049,140 | 9/1991 | Brenner et al. | 604/266 |
| 5,470,320 | 11/1995 | Tiefenbrun et al. | 604/174 |
| 5,922,022 | 7/1999 | Nash et al. | 623/1 |

OTHER PUBLICATIONS

Johnson & Johnson Medical Inc. ad for Surgicel.

*Primary Examiner*—Michael Buiz
*Assistant Examiner*—Vy Q. Bui
*Attorney, Agent, or Firm*—Timothy L. Scott; Philip S. Lyren; Kenneth S. Barrow

[57] ABSTRACT

A device and method are disclosed for reinforcing an anastomotic site (24). The device (14) includes a body (16) and a cuff (18). The body (16) is formed to receive a vascular graft (10). The cuff (18) is coupled to the body (16) and is formed to couple to a target vessel (22) proximate the anastomotic site (24) and to engage the anastomotic site (24). According to one aspect, the cuff (18) is impregnated with medication (30) to be delivered directly to the anastomotic site (24). According to another aspect, the cuff (18) has an adhesive surface (34) for affixation to the target vessel (22).

24 Claims, 3 Drawing Sheets

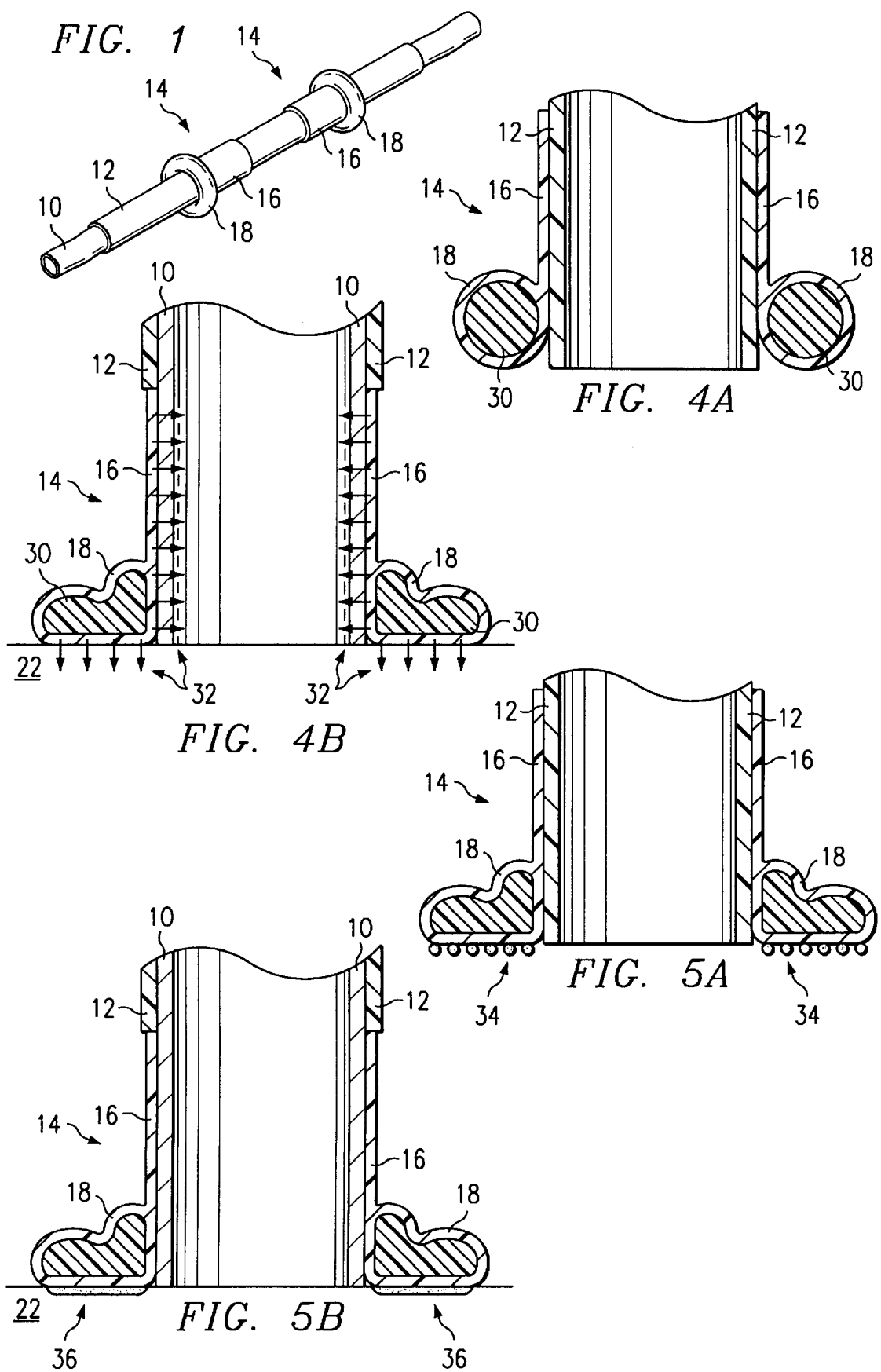

DEVICE AND METHOD FOR REINFORCING AN ANASTOMOTIC SITE

BACKGROUND OF THE INVENTION

Vascular anastomosis involves the attachment of vascular grafts to vessels in a patient. One type of anastomosis is an end-to-side anastomosis which generally involves attaching an end of a graft to a side wall of a target vessel at an opening in the side wall. Another type is an end-to-end anastomosis which generally involves attaching the end of a graft to the end of a target vessel. Typically, in these procedures, the attachment is accomplished by sutures or staples. Some conventional devices and methods for anastomosis are disclosed and described, for example, in U.S. Pat. Nos. 3,774,615; 4,368,736; 4,523,592; 4,607,637; and 4,907,591. One procedure that involves vascular anastomosis is coronary artery bypass surgery where an anastomosis is formed between a vascular graft and the ascending aorta.

Artificial devices are sometimes used to reinforce the vascular graft and the anastomotic site. For example, sleeves are often used to surround and reinforce the vascular graft. Further, absorbable patches can be used to stop anastomotic leakage and deliver antibiotics to inhibit bacterial growth (e.g., SURGICEL and SURGICEL NU-KNIT absorbable hemostat available from JOHNSON & JOHNSON MEDICAL INC.). The delivery of medication to the anastomotic site can increase the success of tissue healing and prevent anastomotic hyperplasia.

However, using conventional devices and methods, it can be difficult to locate an implantable prosthesis for reinforcing an anastomotic site in close proximity to the site due to the unusual geometry. This can be made even more difficult where a sleeve is used to reinforce the vascular graft, which generally must be trimmed to fit the particular length needed. Further, it can be difficult to locate medication delivery in close proximity to the anastomotic site.

SUMMARY OF THE INVENTION

In accordance with the present invention, a device and method for reinforcing an anastomotic site are disclosed that provide significant advantages over prior reinforcement devices and methods.

According to one aspect of the present invention, a device is provided that includes a body and a cuff. The body is formed to receive a vascular graft. The cuff is coupled to the body and is formed to couple to a target vessel proximate the anastomotic site and to engage the anastomotic site. In one embodiment, the cuff is impregnated with medication to be delivered directly to the anastomotic site. According to another embodiment, the cuff has an adhesive surface for affixation to the target vessel.

According to another aspect of the present invention, a method is disclosed for reinforcing an anastomotic site. The method includes positioning a device at an anastomotic site. A cuff of the device is coupled to a target vessel proximate the anastomotic site and engages the anastomotic site. In one embodiment, delivery of medication impregnated in the cuff is initiated such that the medication is delivered directly to the anastomotic site. According to another embodiment, the cuff assembly is coupled to the target vessel by activating an adhesive surface of the cuff.

A technical advantage of the present invention is the ability to directly support and protect an anastomotic site using an implantable prosthetic device which attaches directly to the anastomotic site.

It is also a technical advantage of the present invention to deliver medication, such as an antibiotic, impregnated in the device directly to the interface between the vascular graft and the target vessel at the anastomotic site.

Another technical advantage is the ability to couple the device in place using an adhesive surface on a cuff of the device. The adhesive can be activated, for example, after the device is positioned proximate the anastomotic site. The adhesive can reduce the duration of surgery by eliminating the need to suture or staple the cuff assembly in place.

A further technical advantage of the present invention is its ease of use in combination with a sleeve to protect the vascular graft by accommodating graft and sleeve trimming.

Other technical advantages of the present invention should be apparent to one of ordinary skill in the art in view of the specification, drawings and claims.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein:

FIG. 1 is a diagram of one embodiment of devices for reinforcing an anastomotic site according to the present invention;

FIGS. 4A and 4B are cross section diagrams of one embodiment of a device for reinforcing an anastomotic site according to the present invention;

FIGS. 5A and 5B are cross section diagrams of another embodiment of a device for reinforcing an anastomotic site according to the present invention;

DETAILED DESCRIPTION OF THE INVENTION

Figure 3:
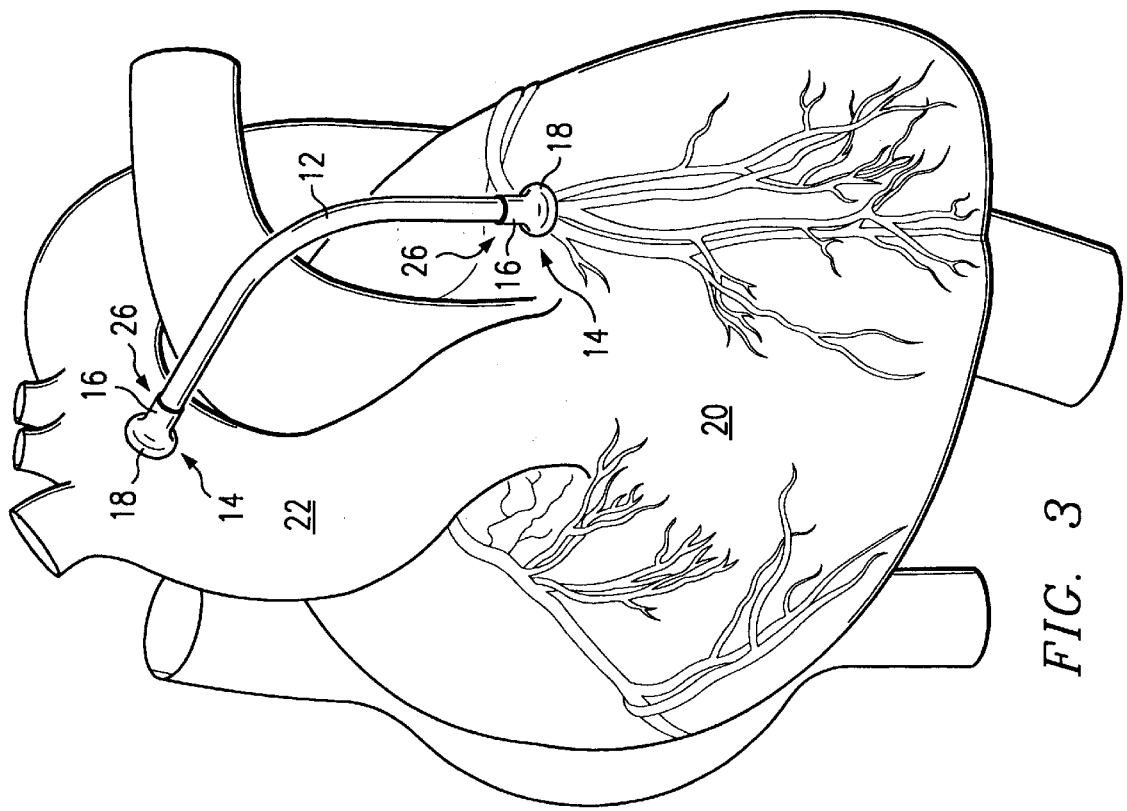
FIG. 3 is a diagram of one embodiment of reinforcing the anastomotic sites of FIG. 2 using the devices of FIG. 1 according to the present invention.

FIG. 1 is a diagram of one embodiment of devices for reinforcing an anastomotic site according to the present invention. Typically, the anastomotic site to be reinforced is an end-to-side anastomosis connecting a vascular graft 10 to a target vessel, such as an artery. However, other types of anastomotic sites, such as end-to-end sites, are possible. As shown in FIG. 1, vascular graft 10 is generally tubular in shape and has two ends. Each end of vascular graft 10 is to be coupled to an opening in the side of a target vessel forming an anastomotic site. For example, vascular graft 10 can be used in a coronary artery bypass procedure.

In the embodiment of FIG. 1, vascular graft 10 extends through a flexible sleeve 12 where sleeve 12 is generally tubular and provides reinforcement for vascular graft 10 after implantation. Devices 14 receive vascular graft 10 and sleeve 12 and will be used to reinforce the anastomotic sites after implantation of vascular graft 10. Each device 14 comprises a body 16 and a cuff 18. Each body 16 is generally tubular and is formed to receive vascular graft 10 and to couple to sleeve 12. Each cuff 18 is coupled to respective body 16 and is generally ring-shaped and formed to engage an anastomotic site. Bodies 16 and cuffs 18 can be separate components or can be formed integral with one another.

As shown, vascular graft 10 extends through sleeve 12 and devices 14. Each device 14 can be positioned in the center portion of vascular graft 10 prior to and during anastomosis of vascular graft 10 in the patient. After forming the anastomosis of vascular graft 10, each device 14 can be moved down over the anastomosis proximate the anastomotic site. Then, each cuff 18 can be coupled, for example using sutures or staples, to engage the anastomotic site, and each body 16 can be coupled to sleeve 12. Devices 14 then provide reinforcement for the anastomotic sites, and sleeve 12 provides reinforcement for vascular graft 10.

In one embodiment, cuff 18 is impregnated with medication for direct delivery at the anastomotic site. The medication can include growth factors, antibiotics and medication to inhibit thrombus formation. The medication can be carried, for example, by a polymer with medication attached or by micro-spheres with medication held inside. Delivery of the medication can then be initiated by compressing cuff 18 after it has engaged the anastomotic site or through time-release mechanisms.

In another embodiment, rather than sutures or staples, cuff 18 can be coupled in place using an adhesive to seal and affix cuff 18 in place. For example, the adhesive can be a biological glue, such as a fibrin based glue, which is activated during surgery when needed by the surgeon. The activation can be triggered, for example, by fluids, such as water or blood. Alternatively, a synthetic glue such as cyanoacrylates or ultra-violet light cured adhesives could be used.

Figure 2:
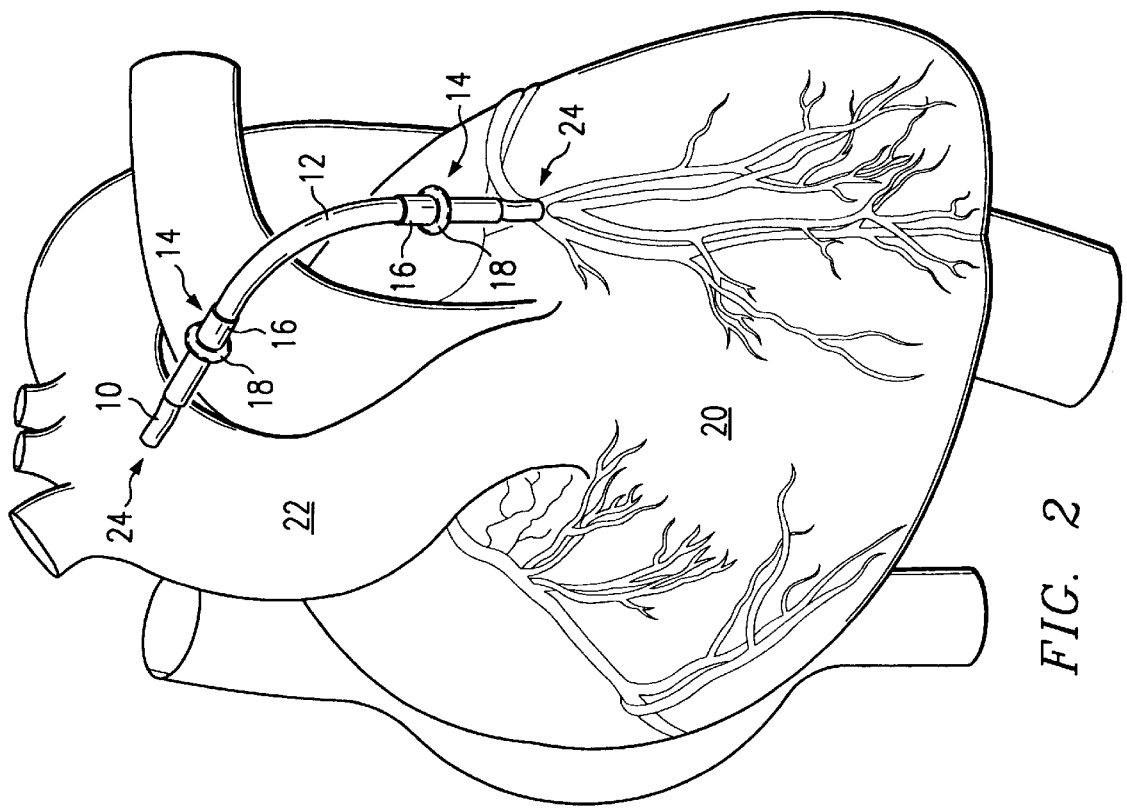
FIG. 2 is a diagram of one embodiment of an arterial bypass where each anastomotic site will be reinforced according to the present invention.

FIG. 2 is a diagram of one embodiment of an arterial bypass where each anastomotic site will be reinforced according to the present invention. In this embodiment, vascular graft 10 provides a bypass between an artery on the surface of heart 20 and aorta 22. Vascular graft 10 is coupled to each receiving artery at anastomotic sites 24. In this case, anastomotic sites 24 are end-to-side anastomotic sites. After formation, anastomotic sites 24 will be reinforced using devices 14 which will remain in place as prosthetic devices. Sleeve 12 will provide reinforcement for vascular graft 10.

FIG. 3 is a diagram of one embodiment of reinforcing anastomotic sites 24 of FIG. 2 using devices 14. As shown, devices 14 have been positioned proximate each anastomotic site 24 such that each cuff 18 is coupled to and engages the associated anastomotic site 24. Each body 16 extends from cuff 18 and is coupled to one end of sleeve 12. For example, the ends of sleeve 12 can be coupled to each body 16 at junctions 26 by suturing or adherence with an adhesive or glue. In this manner, each device 14 reinforces the associated anastomotic site 24.

FIGS. 4A and 4B are cross section diagrams of one embodiment of device 14 for reinforcing an anastomotic site according to the present invention. In FIG. 4A, device 14 includes a body 16 which is coupled to sleeve 12. A cuff 18 is coupled to body 16 and, as shown, is filled or impregnated with an appropriate medication to be delivered to the anastomotic site. For example, medication 30 could provide growth factors, antibiotics and medication to inhibit thrombus formation as mentioned above. In addition, body 16 may be filled or impregnated with a medication. FIG. 4B shows device 14 after implantation, for example, proximate an opening in a side wall of aorta 22. Once in place, cuff 18 or body 16 can be activated (e.g., by compression) to initiate delivery of medication 30 to aorta 22 and vascular graft 10, as indicated generally by 32. This provides delivery of medication 30 at the interface between vascular graft 10 and aorta 22 (or other target vessel) which is precisely the point where medication 30 is most needed to help speed the establishment of the anastomosis.

FIGS. 5A and 5B are cross section diagrams of another embodiment of a device 14 for reinforcing an anastomotic site according to the present invention. As shown, device 14 has a body 16 that is coupled to sleeve 12. In this embodiment, cuff 18 has an adhesive surface 34 for affixing cuff 18 to the anastomotic site. Adhesive surface 34 can be formed using a biological glue, such as a fibrin based glue, or other adhesive. In addition, cuff 18 can be coupled to body 16 with an adhesive. FIG. 5B is a diagram of device 14 after implantation, for example, proximate an opening in a side wall of aorta 22. As shown, adhesive surface 34 affixes cuff 18 to aorta 22 (or other target vessel) at locations 36. This allows device 14 to be easily attached to the anastomotic site by having adhesive surface 34 activated and pressed in place.

Figure 6:
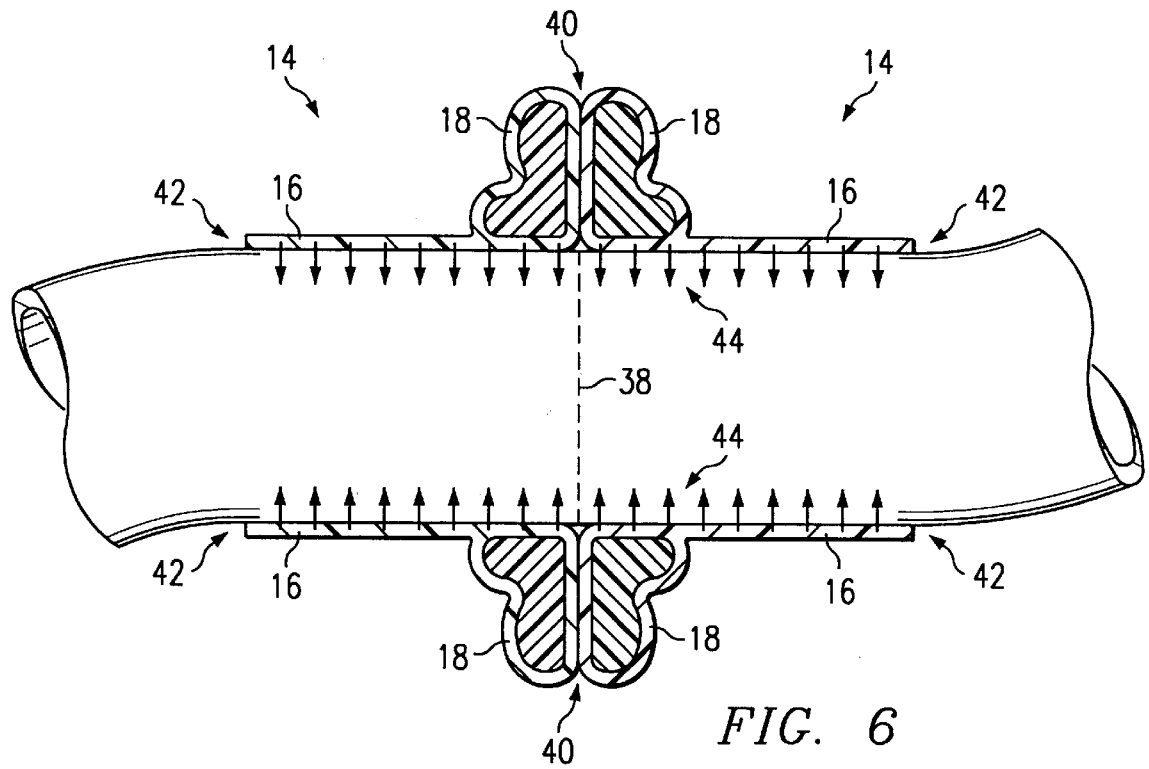
FIG. 6 is a cross section diagram of an end-to-end anastomosis reinforced using devices according to the present invention.

FIG. 6 is a cross section diagram of an end-to-end anastomosis reinforced using devices 14 according to the present invention. As shown, an end-to-end anastomotic site 38 is protected by coupling two devices 14 together at interface 40. Devices 14 can be coupled by sutures or staples or by an adhesive surface as mentioned above. Further, each device 14 could be impregnated with a medication which can be delivered at interface 42, as indicated generally by 44.

Figure 7:
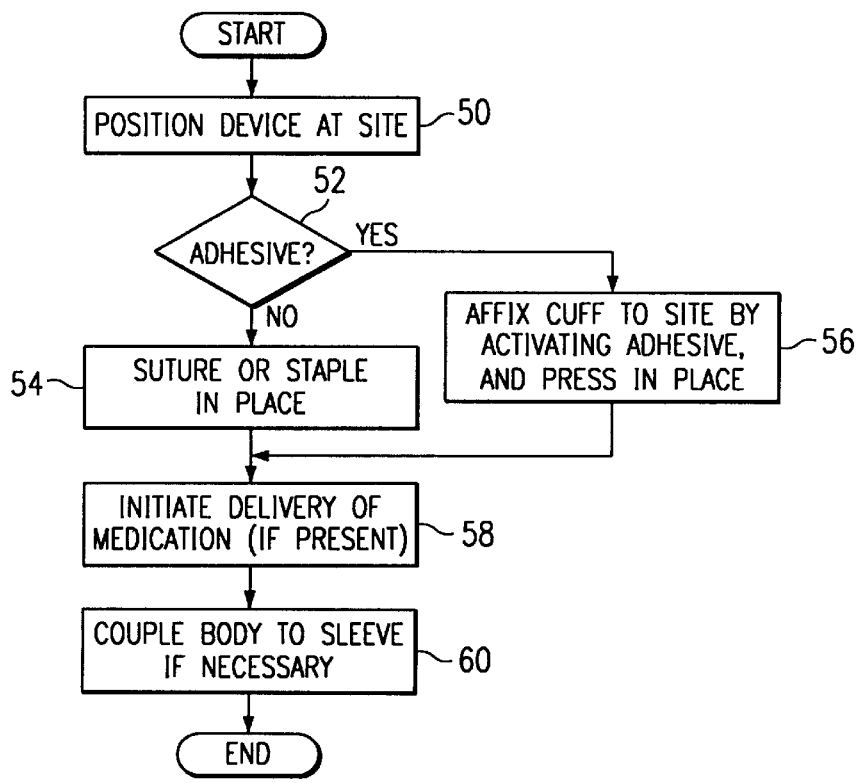
FIG. 7 is a flow chart of one embodiment of a method for reinforcing an anastomotic site according to the present invention.

FIG. 7 is a flow chart of one embodiment of a method for reinforcing an anastomotic site according to the present invention. As shown, in step 50, the reinforcement device is positioned at the anastomotic site. Then, in step 52, it is determined whether the device has an adhesive surface. If not, then the cuff is sutured or stapled in place in step 54. If there is an adhesive surface, in step 56, the cuff is affixed to the anastomotic site by activating the adhesive and pressing the cuff in place. Then, in step 58, delivery of impregnated medication, if present, is initiated. Then, in step 60, the body of the cuff assembly is coupled to the sleeve if the sleeve is present and the body is not already coupled to the sleeve.

Although the present invention has been described in detail, it should be understood that various changes, substitutions and alterations can be made thereto without departing from the spirit and scope of the invention as defined by the appended claims.

What is claimed is:

1. A device for reinforcing an anastomotic site, comprising:

a body formed to receive a vascular graft, said body being movable along the length of the vascular graft; and a cuff coupled to the body and formed to couple to a target vessel proximate the anastomotic site and engage the anastomotic site;

the cuff impregnated with medication to be delivered directly to the anastomotic site.

2. The device of claim 1, wherein the cuff further has an adhesive surface for coupling the cuff to the target vessel.

3. The device of claim 1, wherein the cuff is formed to be sutured to the target vessel.

4. The device of claim 1, wherein the target vessel is an artery.

5. The device of claim 1, wherein the body is formed to be coupled to a sleeve by suturing the body to a first end of the sleeve.

6. The device of claim 1, wherein the body is formed to be coupled to a sleeve by adhering the body to a first end of the sleeve.

7. The device of claim 1, wherein the anastomotic site is an end-to-side site.

8. The device of claim 1, wherein the anastomotic site is an end-to-end site.

9. A device for reinforcing an anastomotic site, comprising:

a body formed to receive a vascular graft, said body being movable along the length of the vascular graft; and a cuff coupled to the body and formed to couple to a target vessel proximate the anastomotic site and engage the anastomotic site;

the cuff comprising an adhesive surface for affixation to the target vessel receiving the vascular graft.

10. The device of claim 9, wherein the cuff further is impregnated with medication to be delivered directly to the anastomotic site.

11. The device of claim 9, wherein the target vessel is an artery.

12. The device of claim 9, wherein the body is formed to be coupled to a sleeve by suturing the body to a first end of the sleeve.

13. The device of claim 9, wherein the body is formed to be coupled to a sleeve by adhering the body to a first end of the sleeve.

14. The device of claim 9, wherein the anastomotic site is an end-to-side site.

15. The device of claim 9, wherein the anastomotic site is an end-to-end site.

16. A method for reinforcing an anastomotic site, comprising:

positioning a device at an anastomotic site, the device comprising a body receiving a vascular graft, said body being movable along the length of the vascular graft, and a cuff coupled to the body;

coupling the cuff to a target vessel proximate the anastomotic site; and initiating delivery of medication impregnated in the cuff such that the medication is delivered directly to the anastomotic site.

17. The method of claim 16, wherein coupling comprises affixing the cuff assembly to the target vessel by activating an adhesive surface of the cuff.

18. The method of claim 16, wherein coupling comprises suturing the cuff to the target vessel.

19. The method of claim 16, further comprising coupling a sleeve to the body of the device distal to the anastomotic site.

20. The method of claim 19, wherein the sleeve is coupled to the body by suturing the body to a first end of the sleeve.

21. The method of claim 19, wherein the sleeve is coupled to the body by adhering the body to a first end of the sleeve.

22. The method of claim 19, wherein the sleeve is coupled to the body by forming the body to be integral with a first end of the sleeve.

23. The method of claim 16, wherein the anastomotic site is an end-to-side site.

24. The method of claim 16, wherein the anastomotic site is an end-to-end site.

* * * * *